US00PP21821P3

(12) United States Plant Patent
Ina

(10) Patent No.: US PP21,821 P3
(45) Date of Patent: Mar. 29, 2011

(54) *MANDEVILLA* PLANT NAMED 'RITA MARIE OTWELL GREEN'

(50) Latin Name: *Mandevilla hybrida*
Varietal Denomination: Rita Marie Otwell Green

(75) Inventor: Kazuyoshi Ina, Aichi-ken (JP)

(73) Assignees: James Mitchell Green, Haines City, FL (US); James Mitchell Green, Jr., Haines City, FL (US); Rita Marie Green, Haines City, FL (US)

( * ) Notice: Subject to any disclaimer, the term of this patent is extended or adjusted under 35 U.S.C. 154(b) by 0 days.

(21) Appl. No.: 12/218,156

(22) Filed: Jul. 11, 2008

(65) Prior Publication Data

US 2010/0011475 P1 Jan. 14, 2010

(51) Int. Cl.
*A01H 5/00* (2006.01)

(52) U.S. Cl. ..... Plt./232

(58) Field of Classification Search ..... Plt./232
See application file for complete search history.

(56) References Cited

U.S. PATENT DOCUMENTS

| | | | | |
|---|---|---|---|---|
| PP8,479 | P | 11/1993 | Henny | Plt./232 |
| PP8,842 | P | 7/1994 | Henny | Plt./232 |
| PP10,095 | P | 11/1997 | Henny | Plt./232 |
| PP10,329 | P | 4/1998 | Wells | Plt./232 |
| PP10,413 | P | 5/1998 | Alston | Plt./232 |
| PP10,611 | P | 9/1998 | Alston | Plt./232 |
| PP10,653 | P | 10/1998 | Gray | Plt./232 |
| PP11,624 | P | 11/2000 | Henny | Plt./232 |
| PP11,787 | P2 | 2/2001 | Green et al. | Plt./232 |
| PP12,123 | P2 | 10/2001 | Sperling | Plt./232 |
| 6,300,547 | B1 | 10/2001 | Green et al. | 800/323 |
| PP12,238 | P2 | 11/2001 | Gray | Plt./232 |
| PP12,813 | P2 | 7/2002 | Gray | Plt./232 |

*Primary Examiner*—Kent L Bell
(74) *Attorney, Agent, or Firm*—Woodcock Washburn LLP

(57) ABSTRACT

A new and distinct cultivar of *Mandevilla* plant named 'Rita Marie Otwell Green', characterized by a full double flower having light pink and white-splashed petals.

1 Drawing Sheet

BACKGROUND OF THE INVENTION

Figure 1:
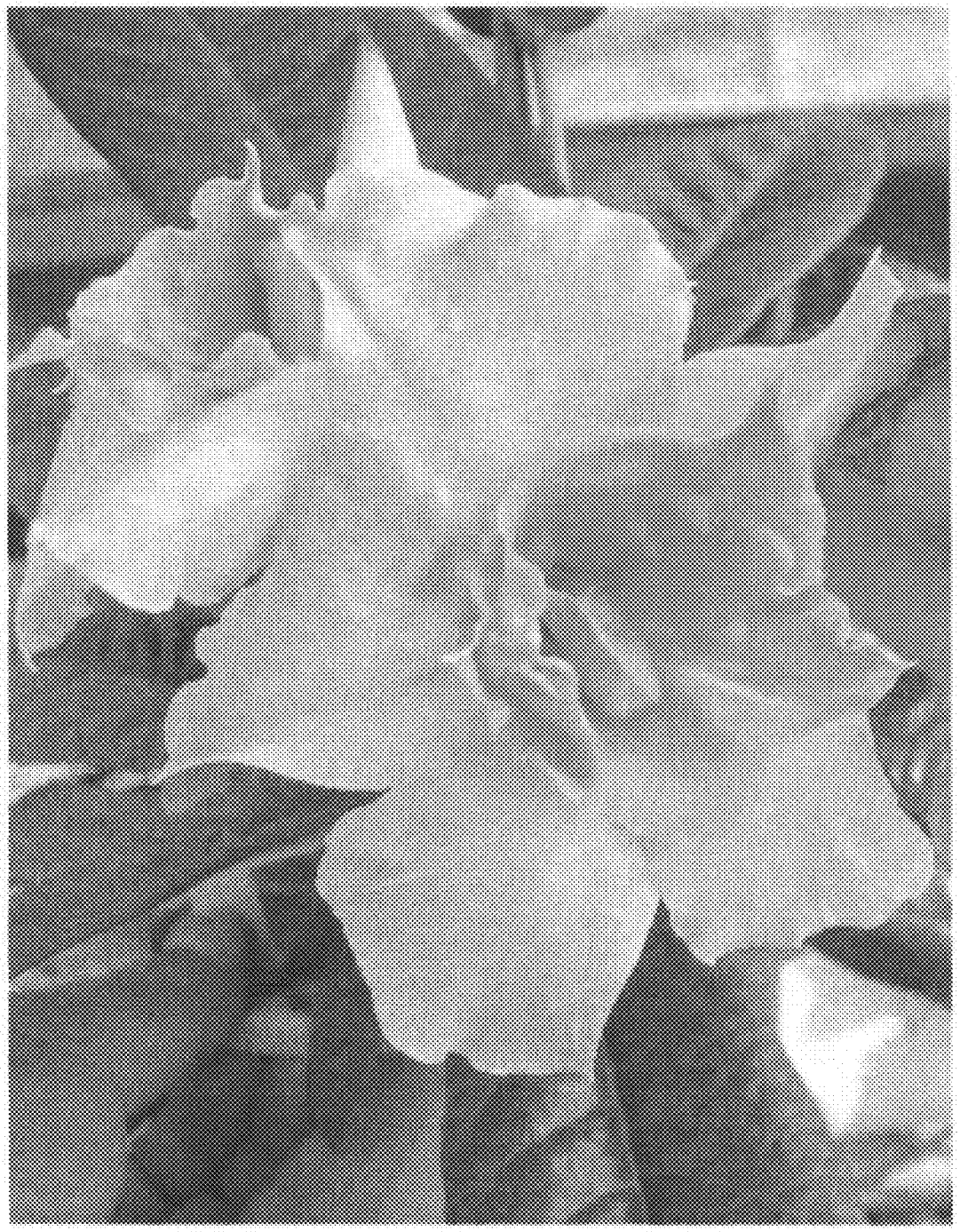

The present invention relates to a new and distinct cultivar of *Mandevilla*, botanically known as *Mandevilla hybrida* and hereinafter referred to by the name 'Rita Marie Otwell Green'.

Botanical designation: *Mandevilla hybrida.*

Cultivar denomination: 'Rita Marie Otwell Green'.

The new *Mandevilla* is a naturally-occurring branch mutation of the *Mandevilla hybrida* cultivar 'Rita Marie Green', disclosed in U.S. Plant Pat. No. 11,787. The new *Mandevilla* was discovered and selected by the Inventor from within a population of plants of the cultivar 'Rita Marie Green' in a controlled environment in Tahara-city Aichi, Japan in June, 2004.

Asexual reproduction of the new cultivar by cuttings in Tahara-city Aichi, Japan since June, 2004, has shown that the unique features of this new Mandevilla are stable and reproduced true to type in successive generations.

SUMMARY OF THE INVENTION

Plants of the cultivar 'Rita Marie Otwell Green' have not been observed under all possible environmental conditions. The phenotype may vary somewhat with variations in environment such as temperature and light intensity without, however, any variance in genotype.

The following traits have been repeatedly observed and are determined to be the unique characteristics of 'Rita Marie Otwell Green'. These characteristics in combination distinguish 'Rita Marie Otwell Green' as a new and distinct cultivar:

1. Light pink and white-splashed petals
2. Early flowering

Plants of the new *Mandevilla* differ primarily from plants of the parent, the cultivar 'Rita Marie Green', in flower color as plants of the cultivar Rita Marie Otwell Green have light pink-colored flowers compared with darker pink color flowers of 'Rita Marie Green'.

Plants of the new *Mandevilla* can be compared to plants of the Mandevilla cultivar 'Rita Marie Green', disclosed in U.S. Plant Pat. No. 11,787. In side-by-side comparisons conducted by the Inventor in Tahara-city Aichi, Japan, plants of the 'Rita Marie Otwell Green' differed from plants of the cultivar 'Rita Marie Green' in the following characteristics:

1. Plants of the new *Mandevilla* and the cultivar 'Rita Marie Green' differ in flower color.
2. Plants of the new Mandevilla are earlier flowering than the cultivar 'Rita Marie Green'.
3. The number of opened flowers in the new *Mandevilla* is more than 'Rita Marie Green', even in the early flowering stage.

The new plant has been propagated from cuttings taken from the parent plant and from progeny produced from such cuttings. My new variety, 'Rita Marie Otwell Green,' has been grown from at least four successive generations of cuttings and each generation has only generated plants that express flowers having the lighter pink color than the parent plant 'Rita Marie Green' (i.e. a first cutting has been taken grown to maturity and then used to provide the cutting for the next generation).

BRIEF DESCRIPTION OF THE PHOTOGRAPH

The accompanying colored photograph illustrates the overall appearance of the new cultivar showing the colors as true as it is reasonably possible to obtain in colored reproductions of this type. Colors in the photographs may differ slightly from the color values cited in the detailed botanical description which accurately describe the actual colors in the new *Mandevilla*.

FIG. 1 is a view of the double flower bloom of 'Rita Marie Otwell Green' showing the double flower structure having light pink and white-splashed petals.

DETAILED BOTANICAL DESCRIPTION

The following is a detailed description of the invention based on plants grown at the Inventor's nursery in Tahara-city, Japan. Color descriptions are according to The Royal Horticultural Society Colour Chart 2001 Edition unless otherwise mentioned. Other terminology is used herein in accordance with ordinary dictionary significance or as commonly used by those of ordinary skill in the relevant art, unless otherwise noted.

Plants used for the aforementioned photograph and following description were grown under conditions which closely approximate commercial production conditions during the early Summer season in an indoor nursery in Tahara-city, Aichi, Japan for about six months. During the production of the plants, day temperatures averaged 25 degrees C. and night temperatures averaged 20 degrees C. Botanical classification: *Mandevilla hybrida* cultivar 'Rita Marie Otwell Green'. Parentage: Naturally-occurring branch-mutation of the *Mandevilla hybrida* cultivar 'Rita Marie Green', disclosed in U.S. Plant Pat. No. 11,787.

THE PLANT

*Foliage.*—Slightly darker green than 'Rita Marie Green':

*Type.*—Evergreen, but if the plants suffer from cold (less than 5° C.), they will change into yellowish color.

*Shape.*—Elliptic (linear to oblong). Apex: Long to short acuminate tip. Base: Cordate.

*Length.*—Variable from about 9.5 cm to 15 cm.

*Width.*—Variable from about 4 cm to 8 cm.

*Color.*—Upper foliage: Yellow green group R.H.S. 146D. Lower foliage: Green group R.H.S. 137A to yellow-green group R.H.S. 147A.

*Arrangement on stem.*—Opposite.

*Margins.*—Entire.

*Habit.*—The 'Rita Marie Otwell Green' variety has a vigorous twining habit and is an ideal semi-tropical creeper. A mature plant of the variety 'Rita Marie Otwell Green' has twining stems 2 meters long and produces leaves that are large and glossy.

*Disease Resistance.*—The 'Rita Marie Otwell Green' variety is not known to be unusually tolerant to any pathogens.

*Frost Tolerance.*—The 'Rita Marie Otwell Green' variety is tolerant to temperatures as low as approximately 5 degree. C.

*Fragrance.*—Flowers of the 'Rita Marie Otwell Green' variety have a slight sweet fragrance.

Flowers:

*Arrangement.*—Axillary racemes.

*Color.*—Upper surface of petals. Corolla and petaloids: Red-purple group RHS. N74B and N74C at the beginning of flowering, the colors might change into red-purple group RHS 69A and purple group RHS 75D during the flowering time, and subsequently, into purple group RHS 76D at fully-opened flower stage. The randomly splashed color is red purple group RHS 69D and purple group RHS 76D. The flowers also have white splashes that are generally 1.5 to 2.5 inches long and 0.375 to 0.75 inches wide. Petaloids (within throat): Slight striations of red-purple group 58B and 58C and yellow group RHS. 2A within 1 cm of base of inner throat. Corolla (within throat): Yellow group RHS. 2A within 2 cm of base of inner throat. Underside of petals: Red-purple group RHS. N74B, N74C, and 69D (splash color) mixed with red-purple RHS. group 69A, and purple group RHS75D. Reproductive structures: Style: Generally present, about 8 mm to 11 mm in length. Stamens: Absent, developed into showy petals. Structure: Overall, funnel shaped. Likely reproductive structures are sterile due to "double" flowers with typical five-numbered stamens converted to petaloids. Outer five parted funnel-shaped corolla limbs. Inner five parted petaloids. Petaloids within the corolla to form a double flower. Corolla: Width: about 10.5 cm to 11.0 cm. Length of throat from calyx to corolla limb attachment: about 4.4 cm to 4.9 cm. Length of corolla from calyx to top of corolla: about 5.5 cm to 6.5 cm. Individual corolla limbs: 4.0 cm to 5.0 cm long, 3.5 cm to 5.5 cm wide. Asymmetrical in shape, ending in a short, abrupt tip. Petaloids (converted stamens): Individual petaloid length: about 4.0 cm to 4.5 cm. Individual petaloid width: about 3.5 cm to 5.0 cm. Petaloid attachment: about 1.5 cm above top of calyx. Petaloid fusion: Fused about 1.5 cm to 2.0 cm at base. Shape: Symmetrical short, abrupt tip. Petaloids are flattened and opened, resembling outer corolla. Length approximately equal to outer corolla, exhibiting a fully double appearance. Petaloids overlay corolla limbs exposing yellow inner base of tube.

The reason for the varied appearance of the double flowers has yet to be determined. However, the light pink double flower characteristics are established and transmitted through succeeding asexual propagations.

It should be noted from observation of 'Rita Marie Otwell Green' that:

The bloom of 'Rita Marie Otwell Green' is lighter than the bloom of the parent Rita Marie Green. The bloom of 'Rita Marie Otwell Green' is pink with splashes of white and lightens as the bloom progresses.

The bloom of 'Rita Marie Otwell Green' appears to start a third set of petals although it is double flowering and not completely triple flowering.

The vining growth habit and dark green leaves are similar to the parent Rita Marie Green.

'Rita Marie Otwell Green' has been observed to flower from spring until frost with continuous flowering.

It has been observed that a plant branch of 'Rita Marie Otwell Green' may produce 15-20 blooms with a well branched plant producing approximately 150 blooms per growing season.

It has been observed that the blooms of 'Rita Marie Otwell Green' last 10-12 days from color buds through bloom.

The leaves and lateral branches of Rita Marie Otwell Green as well as plant height and diameter are similar to 'Rita Marie Green.'

Asexual reproduction of 'Rita Marie Otwell Green' has been performed from cuttings. Other conventional methods for propagation of *Mandevilla* varieties may also be used.

The color denominations in the following information concerning 'Rita Marie Otwell Green' are according to The Royal Horticultural Society Colour Chart 2009 Edition (R.H.S. 2009).

The color of the "white-splash" on the petals of 'Rita Marie Otwell Green' is R.H.S. NN155 B to RHS NN155D. The "white-splash" can fade to R.H.S. 155D.

The leaves of 'Rita Marie Otwell Green' are petiolate with the petiole having a length of about 0.5 to 0.75 inches, a thickness of about 0.0625 to 0.125 inches, a firm texture and color of R.H.S 138 C to R.H.S. 138D.

The mature vines can be up to 15-20 feet long. Near the base of plant the vines may be about 0.375 to 0.625 inches thick and thinning along the length, typically half the thickness of the base at the mid-point of a mature vine and half the thickness of the mid-point near the end of the vine.

Any lateral branches are typically the same as the vine.

When the green buds open to full color buds, the buds are about 2.5 inches in height and about .075 inch in width. The buds have white. R.H.S 155 C to R.H.S. 155D running through the full height of the bud with pink, R.H.S. 62A, running the full height of the bud between the white or vice-versa. The tips of the petals are more pointed than the parent plant and the buds and the blooms have more white and light pink than in the parent plant.

The calyx has a five star shape and its base or bottom is about 0.25 inch. Each of the five stars is about 0.375-0.5 inches long. The base or bottom of the star is about 0.0625 inch.

The peduncle of 'Rita Marie Otwell Green' has a diameter comparable to a pencil lead or penny box match and is strong enough to support 2-3 buds or 3.5 blooms. The texture of the peduncle is very course, not hollow feeling when mashed and the color of the peduncle is medium green, similar to leaves.

What is claimed is:

1. A new and distinct *Mandevilla* plant named 'Rita Marie Otwell Green' as illustrated and described.

* * * * *